(12) United States Patent
Goode et al.

(10) Patent No.: US 7,651,504 B2
(45) Date of Patent: Jan. 26, 2010

(54) DEVICE FOR REMOVING AN ELONGATED STRUCTURE IMPLANTED IN BIOLOGICAL TISSUE

(75) Inventors: Louis B. Goode, Cranberry Township, PA (US); Chun K. Lui, Monroeville, PA (US)

(73) Assignee: Cook Vascular Incorporated, Leechburg, PA (US)

( * ) Notice: Subject to any disclaimer, the term of this patent is extended or adjusted under 35 U.S.C. 154(b) by 583 days.

(21) Appl. No.: 10/358,512

(22) Filed: Feb. 5, 2003

(65) Prior Publication Data

US 2004/0153096 A1    Aug. 5, 2004

(51) Int. Cl.
*A61F 11/00*    (2006.01)
*A61B 17/24*    (2006.01)
(52) U.S. Cl. ....................... 606/113; 606/108
(58) Field of Classification Search ................. 604/322, 604/326, 328, 508, 544; 606/113, 114, 108, 606/106; 607/1, 115, 116
See application file for complete search history.

(56) References Cited

U.S. PATENT DOCUMENTS

| | | | |
|---|---|---|---|
| 4,493,320 A | 1/1985 | Treat | |
| 5,098,440 A * | 3/1992 | Hillstead | ..................... 606/108 |
| 5,318,527 A | 6/1994 | Hyde et al. | |
| 5,342,371 A | 8/1994 | Welter et al. | |
| 5,387,219 A | 2/1995 | Rappe | |
| 5,522,819 A | 6/1996 | Graves et al. | |
| 5,562,678 A | 10/1996 | Booker | |
| 5,823,971 A * | 10/1998 | Robinson et al. | ............. 600/567 |
| 6,068,603 A * | 5/2000 | Suzuki | ........................ 600/565 |
| 6,517,550 B1 * | 2/2003 | Konya et al. | ................. 606/113 |

\* cited by examiner

*Primary Examiner*—(Jackie) Tan-Uyen T. Ho
*Assistant Examiner*—Melissa Ryckman
(74) *Attorney, Agent, or Firm*—Brinks Hofer Gilson & Lione

(57) ABSTRACT

A snare-type device for removing an elongated structure such as, for example, a pacemaker lead. The device first includes a sheath having a first lumen formed therein, the first lumen having a distal end and being dimensioned to receive the elongated structure therein, and being adapted to allow advancement of the sheath along the elongated structure. The sheath also has second and third parallel lumens formed therein, all of the first, second and third lumens being unitarily formed in the sheath. The device also includes a snare contained in the second and third lumens in the sheath. The snare has a snare loop extending out of the second and third lumens, at and generally extending around the distal end of the first lumen.

19 Claims, 2 Drawing Sheets

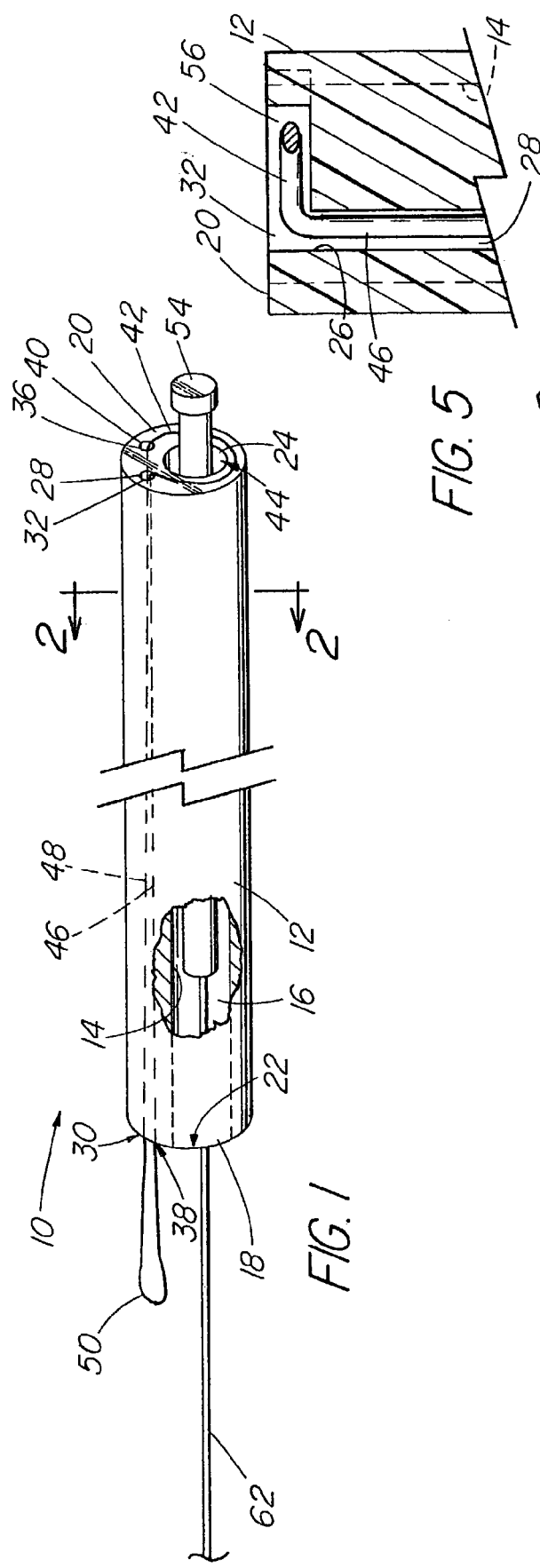
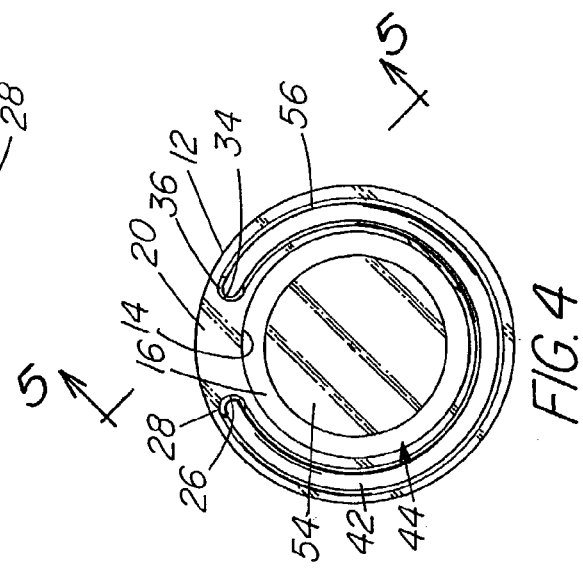
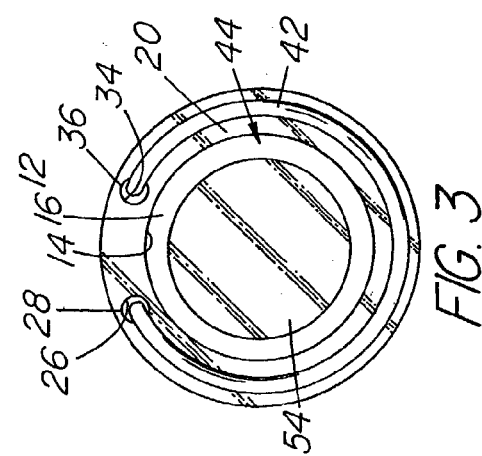
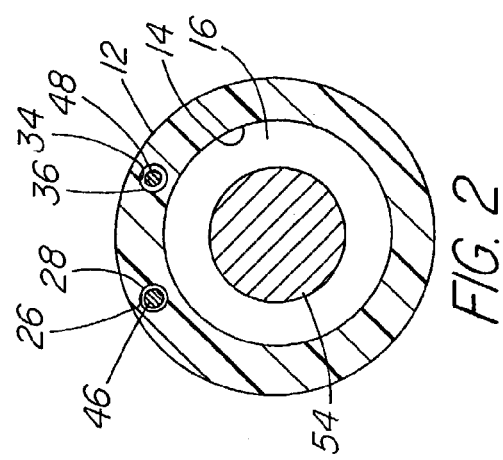

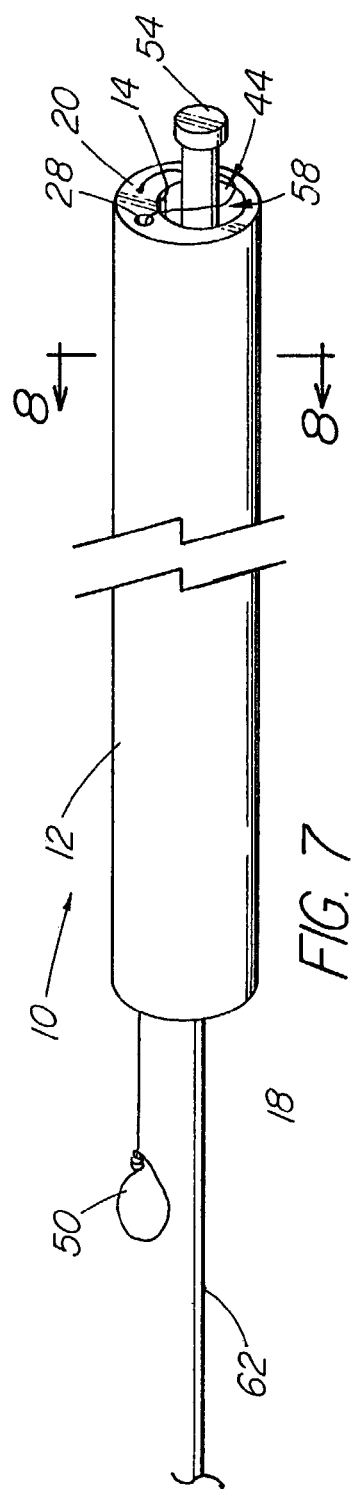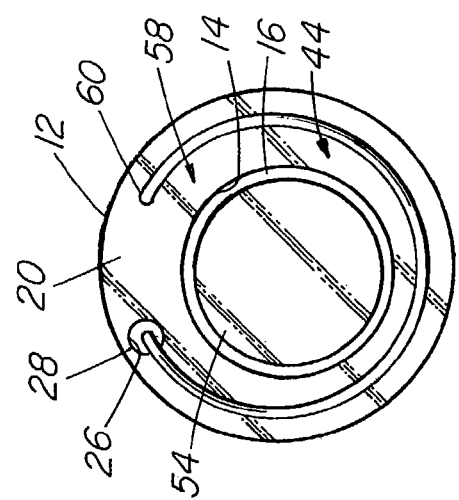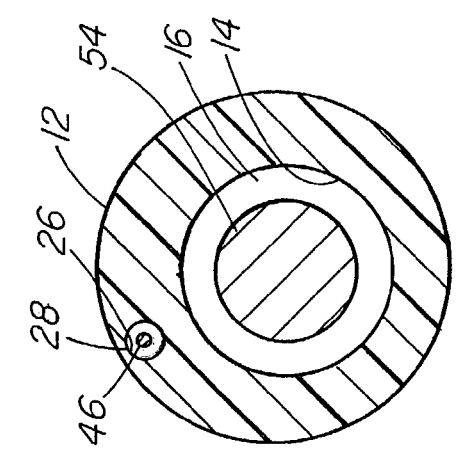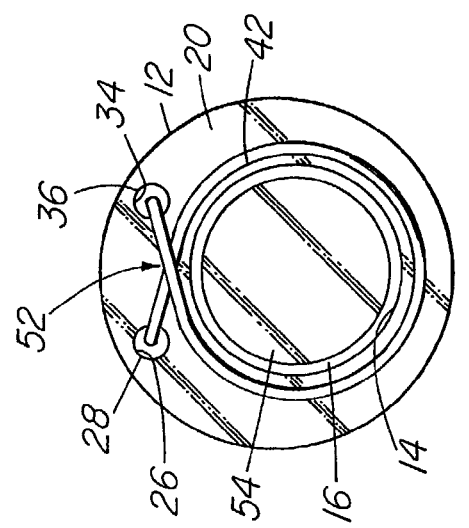

DEVICE FOR REMOVING AN ELONGATED STRUCTURE IMPLANTED IN BIOLOGICAL TISSUE

TECHNICAL FIELD

This invention relates generally to medical devices, and more particularly to devices for engaging and removing or retrieving an elongated structure which has previously been implanted in biological tissue, for example, a cardiac electrical lead (such as a pacemaker or defibrillator lead) implanted in the vascular or other system of a human or veterinary patient.

BACKGROUND OF THE INVENTION

A variety of medical treatments and surgical methods entail implanting an elongated structure in the body of a human or veterinary patient. Examples of such elongated structures include catheters, sheaths and cardiac electrical leads (such as pacemaker leads and defibrillator leads), and a variety of other devices. Over time, it may become necessary or desirable to remove such an elongated structure from the body of the patient. However, problems may be encountered in attempting removal of an elongated structure implanted in biological tissue.

For example, a heart pacemaker is typically implanted in a subcutaneous tissue pocket in the chest wall of a patient, and a pacemaker lead positioned in the vascular system of the patient, extending from the pacemaker and through a vein into a chamber of the patient's heart. The pacemaker lead commonly includes a coiled structure such as an electrical wire coil for conducting electrical signals (such as stimulating and/or sensing signals) between the pacemaker and the heart. Defibrillator leads are generally similar and, like pacemaker leads, are located about the heart, but are affixed both internally and externally of the heart. A typical lead includes one or more coaxial or lateral helical wire coils having a hollow inner passageway that extends the entire length of the wire coil or coils. The wire coils are surrounded by an electrically insulating material such as a flexible tube, sheath or coating. The insulating material may be silicone or polyurethane, and serve simultaneously to protect the wire coils from body fluids and to insulate the wire coils from one another.

While cardiac electrical leads typically have a useful life of many years, over time pacemaker and defibrillator leads unfortunately become encapsulated by fibrotic tissue against the heart itself or the wall of the vein, or against other surrounding tissue. Encapsulation is especially encountered in areas where the velocity of the flow of blood is low. The fibrotic tissue is tough and makes it difficult to remove the lead from the area of the heart without bleeding or other trauma to the area. For example, when small diameter veins through which a pacemaker lead passes become occluded with fibrotic tissue, separating the lead from the vein can cause severe damage to the vein or even destruction of it. Furthermore, separation of the lead from the vein is usually not possible without restricting or containing movement of the lead, that is, fixing the lead in position with respect to the patient, in particular, with respect to the patient's vein.

To avoid this and other possible complications, some useless pacemaker or other leads are simply left in the patient when the pacemaker or defibrillator is removed or replaced. However, such a practice can incur the risk of an undetected lead thrombosis, which can result in stroke, heart attack, or pulmonary embolism. Such a practice can also impair heart function, as plural leads can restrict the heart valves through which they pass.

There are of course many other reasons why removal of a useless lead is desirable. For example, if there are too many leads positioned in a vein, the vein can be obliterated. Multiple leads may be incompatible with one another, interfering with their pacemaking or defibrillating function. Of course, an inoperative lead can migrate during introduction of an adjacent second lead, and mechanically induce ventricular arrhythmia. Other potentially life-threatening complications can require the removal of the lead as well. For example, removal of an infected pacemaker lead is desirable, so as to avoid septicemia or endocarditis. Surgical removal of a heart lead in such circumstances often involves open heart surgery, with its accompanying risks, complications and significant costs.

A variety of successful methods and apparatus have been devised as alternatives to open heart surgery for heart lead removal. For example, U.S. Pat. No. 5,697,936 (Shipko et al., Dec. 16, 1997) discloses a device for removing from a patient a previously implanted elongated structure such as a catheter, a sheath, a defibrillator lead, a pacemaker lead or the like. The device disclosed by Shipko et al. includes a snare having one or more proximal or distal loops which can encircle and reversibly grasp either the proximal end or the distal end of the elongated structure to be removed. The device also includes a sheath member for delivering the snare loop or loops to the particular end of the elongated structure which is to be grasped. In some disclosed embodiments for grasping the distal end of the elongated structure, the sheath member is advanced along the elongated structure and separates the structure from any tissue which has encapsulated the structure after its implantation. The snare can be either positioned over or contained within a second sheath located in the sheath member. The patent does not appear to disclose any way for the snare loop or loops to be extended beyond the distal end of the sheath member, however.

Numerous other devices for snaring fragments or foreign bodies have been disclosed. For example, U.S. Pat. No. 5,171,233 (Amplatz et al., Dec. 15, 1992) is directed to a snare-type probe in which kinking of a snare loop is obviated by the use of a shape memory material for the snare. More particularly, the snare is composed of nitinol (nickel-titanium alloy system) wire in a superelastic state, having a transition temperature below the operating temperature of the snare, for example, below body or room temperature. This allows the snare to be manipulated in a relatively severe manner during introduction into a patient, but to recover its desired shape after such manipulation, without kinking or other deformation. The loop of the snare of the device is oriented at an angle with respect to an elongate proximal member on which it is carried.

U.S. Pat. No. 5,562,678 (Booker, Oct. 8, 1996) discloses a reversible snare for grasping and retrieving an article such as a cardiac lead, which includes a retractable closed loop carried by a sheath member adapted for introduction into a patient. The closed loop of the snare is composed of nitinol or another shape memory material and defines a hook adapted to partly encircle the cardiac lead. The snare also includes a threader also carried by the sheath member; the threader is reversibly extendable through the closed loop, like a thread through a needle's eye, so that the hook and threader together fully encircle the lead. Retraction of the closed loop causes the hook and threader to close around the lead and permit its withdrawal into the sheath member. There appears to be no disclosure of any way in which the cardiac lead could be received through only the closed loop of the snare itself.

Finally, U.S. Pat. No. 5,318,527 (Hyde et al., Jun. 7, 1994) is directed to a system for removing an in-place intravascular device (such as a catheter or guidewire) from a patient's body lumen, such as from a coronary artery, in which a catheter or other similar device is advanced through the vascular system alongside the in-place device until its distal end is located at a desired location within the vascular system. The disclosed removal system includes an exchange catheter having a flexible strand which forms a loop at the distal end of the catheter, the loop being adapted to be disposed about the catheter or guidewire that is in-place within the patient. The exchange catheter includes a lumen through which the strand passes and from which the loop extends. The exchange catheter does not appear to be dimensioned or otherwise adapted for receiving the in-place catheter or guidewire within the exchange catheter as the exchange catheter is advanced. To the contrary, it is an express purpose of the disclosed device to maintain access to a region of the body lumen about the distal end of the in-place catheter or guidewire during use of the exchange catheter, and receipt of the in-place device in the exchange catheter would interfere with the desired access to that region.

Each of these devices is subject to its own advantages and drawbacks during use. The devices of Shipko et al. and Booker may be somewhat more complex in structure than might be preferred, since it is usually desirable to employ removal devices having a minimal cross-sectional area. The device of Amplatz et al. may require a disadvantageously high degree of axial and/or rotational manipulation before the loop can be slipped over the distal end of the device to be removed. The device of Hyde et al. purportedly avoids this particular problem by having its loop slipped over the proximal end of the in-place device and tightened about it before the exchange catheter is advanced, but not tightened about the in-place device so much that the exchange catheter cannot be readily advanced over the in-place device, or that the in-place device cannot be readily withdrawn. It should go without saying that the device and procedure of Hyde et al. would not be useful for retrieving an elongated structure which have been left in a patient for any extended time, since encapsulation of the structure would prevent any such advancement of the exchange catheter along the structure. Moreover, kinks or surface defects or irregularities in the in-place device could make it difficult or impossible to achieve a desirably precise degree of tightening of the loop about the in-place device. Such surface defects or irregularities could result from minor amounts of encapsulating tissue which remain on the in-place device after severing of the in-place device from the bulk of the encapsulating tissue, or from defects or breakage of the in-place device itself.

It would be highly advantageous to have a snare-type device for removing from a patient a previously implanted elongated structure (such as a catheter, a sheath, a defibrillator lead, a pacemaker lead or the like) which had a minimal cross-sectional profile. It would also be highly advantageous to have such a device which avoided the need for rotational manipulation of the snare, before closure of the snare loop about the elongated structure, to ensure that the snare loop was in fact positioned at a location allowing it to close about the elongated structure. It would further be highly advantageous to have such a device which could be used to remove an elongated structure which had been in place in a patient for a time long enough to become somewhat encapsulated within the body lumen in which the structure was positioned.

SUMMARY OF THE INVENTION

The foregoing problems are solved and a technical advance is achieved in an illustrative device and method for removing from a human or veterinary patient an elongated structure which has previously been implanted in the patient. More particularly, the device first comprises a sheath having at least two and preferably three lumens formed longitudinally in it. A first one of the lumens is relatively larger in diameter and is dimensioned (that is, sized and structurally arranged and adapted) both to receive the elongated structure within it, and to allow advancement of the sheath along the elongated structure while it is received in the first sheath lumen.

The second lumen (and the third lumen if present) is relatively smaller in diameter and contains a snare, in particular, one leg of a snare. The snare also has a snare loop extending out of the second lumen (as well as out of the third lumen, if present) which is closeable about the elongated structure so as to permit its capture and removal from the patient. The snare loop is positioned at the distal end of the first lumen in the sheath, and extends generally around the distal end of the first lumen, such that the snare loop is automatically positioned around the elongated structure when the structure is received in the first lumen. Such positioning advantageously allows the present invention to avoid the need for rotational manipulation of the snare loop over the distal end of the elongated structure in order to capture it.

The sheath is preferably tubular in shape, with the first, second and third lumens formed in parallel within it. The sheath and its lumens are preferably formed unitarily, for example, by extrusion, such that the sheath and its lumens are constructed as a single piece.

The snare can be a continuous wire circlet received in the second and third lumens in the sheath, or can be a single wire having a distal end anchored to the distal end of the sheath, with a single leg extending through only a second lumen in the sheath. Preferably, the snare loop of the snare is disposed generally perpendicular to the second lumen, extending from the distal end of the second lumen or the second and third lumens. This perpendicular disposition can be maintained by allowing the snare loop to be received in an arcuate groove in the distal end of the sheath, lying about the distal end of the first lumen. Alternatively, this perpendicular disposition can be maintained by composing the snare itself of a shape memory material, such as nickel-titanium (nitinol) alloy. Either arrangement prevents the premature entanglement of the snare loop with the elongated structure, such as during advancement of the sheath along the elongated structure.

The present invention is particularly advantageous over prior snare-type intravascular retrievers in its minimal cross-sectional area and in its good reliability of capture of the elongated structure to be removed or retrieved without the need to rotate the device in order to position the snare loop of the device over the elongated structure to be retrieved.

In a first aspect, then, the present invention is directed to a device for removing an elongated structure implanted in biological tissue, comprising: a sheath having a first wall defining a first lumen therein, the first lumen having a distal end and being dimensioned to receive the elongated structure therein, and being adapted to allow advancement of the sheath along the elongated structure, the sheath also having a second wall defining a second lumen therein; and a snare contained in at least the second lumen in the sheath, the snare having a snare loop extending out of at least the second lumen, at and generally extending around the distal end of the first lumen in the sheath, the snare loop being closeable about the elongated structure when the elongated structure is received in the first lumen of the sheath. The sheath is preferably tubular in shape. "At and generally extending around" the distal end of the first lumen in the sheath means that the snare loop is located at the distal end of the first lumen, and is positioned with respect to the distal end of the first lumen such that the snare loop need not be manipulated (such as by rotation of the sheath) in order to be positioned for the successful capture of the elongated structure positioned in the first lumen, upon closing of the snare loop. Rotation of the device after the elongated structure is captured in the first lumen is, of course, contemplated within the expected use of the device of the present invention.

Preferably, the sheath further has a third wall defining a third lumen therein, the snare being contained in both the second lumen and the third lumen of the sheath. Also preferably, the second and third lumens are coterminal with either or both of the first lumen and the sheath; that is, all of the lumens preferably run the length of the sheath, such that the distal ends of all of the lumens are at the distal end of the sheath. It is further preferred that all of the lumens are disposed in parallel to each other within the sheath, and are unitarily formed in the sheath, that is, the sheath comprises a single piece in which all of the lumens are formed.

The snare preferably comprises at least one leg connected to the snare loop and disposed in the second lumen in the sheath, and more preferably comprises another leg connected to the snare loop and disposed in the third lumen in the sheath. The snare also preferably includes a graspable pull opposite the snare loop.

The snare loop depends generally perpendicularly from the distal ends of the second and third lumens, and from the distal end of the sheath. Conveniently, the snare can be composed of a shape memory material such as nitinol alloy. The snare loop is preferably positioned with respect to the sheath so that during use of the device of the present invention, the snare loop draws the elongated structure against the first wall of the sheath when it is closed about the elongated structure.

In alternative embodiments, the snare loop can cross over itself, and/or the snare loop can be received in a recess in the distal end of the sheath.

In a second aspect, the present invention is directed to a specific combination of the features mentioned above. More particularly, in its second aspect, the present invention is directed to a device for removing an elongated structure implanted in biological tissue, comprising: a sheath having a first wall defining a first lumen therein, the first lumen having a distal end and being dimensioned to receive the elongated structure therein, and being adapted to allow advancement of the sheath along the elongated structure; the sheath also having second and third walls defining second and third parallel lumens therein, the second and third lumens being coterminal with the first lumen and the sheath, and all of the first, second and third lumens being unitarily formed in the sheath; and a snare contained in the second and third lumens in the sheath, the snare having a snare loop extending out of the second and third lumens, at and generally extending around the distal end of the first lumen in the sheath; wherein the snare comprises one leg disposed in the second lumen and another leg disposed in the third lumen, the legs being connected to the snare loop, and a graspable pull connected to the legs of the snare opposite the snare loop; and wherein the snare loop depends generally perpendicularly from distal ends of the second and third lumens, and is closeable about the elongated structure when the elongated structure is received in the first lumen of the sheath.

In a third and final aspect, the present invention is directed to a method for using the device disclosed above. More particularly, in its third aspect, the present invention is directed to a method for removing an elongated structure implanted in biological tissue, carried out with a device comprising: a sheath having a first wall defining a first lumen therein, the first lumen having a distal end being dimensioned to receive the elongated structure therein, being adapted to allow advancement of the sheath along the elongated structure, the sheath also having a second wall defining a second lumen therein; a snare contained in at least the second lumen in the sheath, the snare having a snare loop extending out of at least the second lumen, at and generally extending around the distal end of the first lumen in the sheath, the snare loop being closeable about the elongated structure when the elongated structure is received in the first lumen of the sheath; the method comprising the steps of: positioning the sheath of the device so that the elongated structure is received in the first lumen of the sheath; and closing the snare loop about the elongated structure.

As indicated above, the device of the present invention may possess significant advantages over prior devices for removing an elongated structure such as a catheter, a sheath, a defibrillator lead, a pacemaker lead or the like from a patient. The device of the present invention has a minimal cross-sectional profile, improving the patency of the body lumen in which it is being used, and thereby minimizing the potential for adverse effects upon the patient from impairment of lumen patency during such use. The device of the present invention does not need to be rotated before closure of the snare loop about the elongated structure, to ensure that the snare loop is in fact positioned so as to close about the elongated structure. Rotation of the device after closure of the snare loop about the elongated structure may, of course, be advantageous, and is contemplated within the use of the device of the present invention. Finally, if the device of the present invention is configured so as to have a cutting tip, it can be employed to remove an elongated structure which has been in place in a patient for a time long enough to become somewhat encapsulated within the body lumen in which the structure was positioned. Alternatively, other devices might be used to separate the elongated structure from any encapsulating tissue before use of the device of the present invention; however, since such other devices need not include a snare or the like for the actual retrieval of the elongated structure, the cross-sectional areas of those other devices may similarly be minimized, again allowing the patency of the body lumen to be maximized.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which:

FIG. 1 is a perspective view of the preferred embodiment of the present invention;

FIG. 2 is a cross-sectional view taken along line 2-2 of FIG. 1;

FIG. 3 is an end view of the preferred embodiment of the present invention shown in FIG. 1;

FIG. 4 is an end view of another preferred embodiment of the present invention;

FIG. 5 is a cross-sectional view taken along line 5-5 of FIG. 4;

FIG. 6 is an end view of yet another preferred embodiment of the present invention;

FIG. 7 is a perspective view of another preferred embodiment of the present invention;

FIG. 8 is a cross-sectional view taken along line 8-8 of FIG. 7; and

FIG. 9 is an end view of the preferred embodiment of the present invention shown in FIG. 7.

DETAILED DESCRIPTION

With reference to FIGS. 1 through 3, a first embodiment of a snare-type device 10 according to the present invention is thereshown, useful for removing a previously implanted elongated structure 54 (such as a catheter, a sheath, a defibrillator lead, a pacemaker lead or the like) from a human or veterinary patient, for example, from the vascular system of the patient. For convenience, the elongated structure 54 may have previously been separated from any encapsulating tissue by use of another device, several of such devices being known. Alternatively, it is possible that the device 10 could itself be adapted to perform such severing. Also, for convenience a guide wire or extension 62 may have been previously attached to aid engagement of the device 10 of the present invention with the elongated structure 54.

The device 10 of the present invention first comprises a sheath 12 having a first wall 14 defining a first lumen 16 therein. The sheath 12 is preferably tubular in configuration and is composed of a suitable, flexible medical grade material. The first lumen 16 preferably extends longitudinally through the sheath 12 from the proximal end 18 of the sheath 12 to the distal end 20 of the sheath 12. The first lumen 16 thus has a proximal end 22 and a distal end 24 at the proximal and distal ends 18 and 20 of the sheath 12, respectively, such that the first lumen 16 is coterminal with the sheath 12. The first lumen 16 is dimensioned (that is, it is sized, structured, arranged and adapted) both to receive the elongated structure 54 in it, and to allow advancement of the sheath 12 along the elongated structure 54 (and along the guide wire or extension 62 as well, if present).

The sheath 12 also has at least a second wall 26 defining a second lumen 28 therein, the second lumen 28 preferably extending longitudinally through the sheath 12 from the proximal end 18 of the sheath 12 to the distal end 20 of the sheath 12. The second lumen 28 thus has a proximal end 30 and a distal end 32 at the proximal and distal ends 18 and 20 of the sheath 12, respectively, and at the proximal and distal ends 22 and 24 of the first lumen 16, respectively. The second lumen 28 thus is preferably coterminal with both the first lumen 16 and the sheath 12. In the first preferred embodiment of the present invention, the sheath 12 further has a third wall 34 defining a third lumen 36 in the sheath 12. The third lumen 36 similarly preferably extends longitudinally through the sheath 12 from its proximal end 18 to its distal end 20, such that the third lumen 36 has a proximal end 38 and a distal end 40 at the proximal and distal ends 18 and 20 of the sheath 12, and at the proximal and distal ends 22 and 24 of the first lumen 16, respectively. The third lumen 36 thus is also preferably coterminal with both the first lumen 16 and the sheath 12. The first, second and third lumens 16, 28 and 36 are preferably disposed parallel with one another.

The removal device 10 of the present invention also comprises a snare contained in at least the second lumen 28, for example, a snare 42 contained in the second and third lumens 28 and 36. The snare 42 comprises a snare loop 44 which extends out of at least the second lumen 28, for example, out of both the second and third lumens 28 and 36. The snare loop 44 is located at the distal end 24 of the first lumen 16 and extends generally around the distal end 24 of the first lumen 16, such that the snare loop 44 is automatically positioned about the elongated structure 54 when the elongated structure 54 is received in the first lumen 16 of the sheath 12. The snare 42 comprises one leg 46 disposed in the second lumen 28 and another leg 48 disposed in the third lumen 36, each of the legs 46 and 48 being connected to the snare loop 44. The snare 42 preferably further comprises a graspable pull or handle 50 opposite the snare loop 44, connected to each of the legs 46 and 48. The graspable pull 50 need not be a separate part of the snare 42, but can merely be the bight which extends proximally from the proximal ends 30 and 38 of the second and third lumens 28 and 36, respectively.

The snare loop 44 is closeable about the elongated structure 54 when the elongated structure 54 is so received in the first lumen 16. Preferably, the snare loop 44 is positioned so as to draw the elongated structure 54 against the first wall 14 of the sheath 12 upon closure of the snare loop 44. The snare loop 44 preferably depends generally perpendicularly from the distal ends 32 and 40 of the second and third lumens 28 and 36, respectively. Such a perpendicular dependency can be maintained in several ways. Conveniently, the snare 42 can be composed of a shape memory material, such as nitinol alloy or another suitable material, with the snare loop 44 bent to an appropriate angle. Alternatively, as shown in FIGS. 4 and 5, an arc-shaped recess 56 can be provided in the distal end 20 of the sheath 12. In either case, the perpendicular dependency of the snare loop 44 prevents premature entanglement of the snare loop 44 with the elongated structure 54 during advancement of the sheath 12 along the elongated structure 54.

Of course, other arrangements for the snare 42 and snare loop 44 are contemplated within the present invention. For example, the snare loop 44 need not be disposed in a circularly arcuate manner. Instead, the snare loop 44 may be arranged so that it crosses over itself at a location near the distal ends 32 and 40 of the second and third lumens 28 and 36, respectively. The resulting shape is shown in FIG. 6 and is designated as snare loop 52.

Indeed, the snare of the device 10 of the present invention need not itself be a continuous loop. As shown in FIGS. 7 through 9, an alternative snare 58 is thereshown having only a single leg 46 extending through the second lumen 28 in the sheath 12. The snare 58 has a distal end 60 which is affixed directly to the distal end 20 of the sheath 12. In such a case, the third lumen 36 can be omitted from the sheath 12, as shown.

Without regard to the precise configuration of the snare 42 or 58, however, use of the device 10 for removing a previously implanted elongated structure 54 from a human or veterinary patient is straightforward. The elongated structure 54 is first prepared for removal, for example, by severing from any encapsulating tissue, or by attachment of a guide wire or extension 62. Such severing may be carried out with a different apparatus; however, it is possible that the sheath 12 of the device 10 of the present invention could include a cutting tip on its distal end 20, which would act to sever the elongated structure 54 from any encapsulating tissue. In any case, the sheath 12 of the device 12 is positioned over the guide wire or extension 62 such that the guide wire or extension 62 passes through the first lumen 16 in the sheath 12. The sheath 12 is then advanced distally, first along the guide wire or extension 62 and then along the elongated structure 54 itself, until the distal end 20 of the sheath 12 is positioned adjacent to the distal end of the elongated structure 54, and the elongated structure 54 is received fully (or, at least, substantially fully) within the first lumen 16 in the sheath 12. The pull 50 is then grasped and drawn proximally so as to close the snare loop 44

(or 52) about the elongated structure 54. The device 10 and the elongated structure 54 can then be proximally withdrawn from the patient as a single unit. Rotation of the sheath 12 with respect to the elongated structure 54 after closure of the snare loop 44 (or 52) may provide a more secure engagement of the snare loop 44 (or 52) with the elongated structure 54.

In view of the foregoing, it should be clear that the present invention provides a device 10 for removing or retrieving previously implanted elongated structures which possesses significant advantages over prior devices for that purpose. For example, the device 10 of the present invention has a minimal cross-sectional profile, improving the patency of the body lumen in which it is being used, and thereby minimizing the potential for adverse effects upon the patient from impairment of lumen patency during such use. The device 10 of the present invention does not need to be rotated before closure of the snare loop 44 or 52 about the elongated structure, to ensure that the snare loop is in fact positioned so as to close about the elongated structure; the indicated positioning of the snare loop 44 or 52 with respect to the distal end 24 of the first lumen 16 assures that proper capture of the elongated structure 54 occurs automatically. (Subsequent rotation of the device 10 after closure of the snare loop 44 or 52 about the elongated structure 54 may be advantageous, and is of course contemplated within the use of the device 10 of the present invention.) Finally, the device 10 of the present invention might be configured so as to have a cutting tip at the distal end 20 of the sheath 12, such that the device 10 can be employed to remove an elongated structure 54 which has been in place in a patient for a time long enough to become somewhat encapsulated within the body lumen in which the structure was positioned. Other devices can instead be used to separate the elongated structure 54 from any encapsulating tissue before use of the device 10 of the present invention; however, since such other devices need not include a snare or the like for the actual retrieval of the elongated structure, the cross-sectional areas of those other devices may similarly be minimized, again allowing the patency of the body lumen to be maximized.

The details of the construction or composition of the various elements of the removal device 10 of the present invention not otherwise disclosed are not believed to be critical to the achievement of the advantages of the present invention, so long as the elements possess the strength or mechanical properties needed for them to perform as disclosed. The selection of any such details of construction are believed to be well within the ability of one of even rudimentary skills in this area, in view of the present disclosure.

INDUSTRIAL APPLICABILITY

The present invention is useful for removing from a patient a previously implanted elongated structure, such as a catheter, a sheath, a pacemaker lead, a defibrillator lead or the like, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A device for removing an elongated medical apparatus previously implanted in biological tissue for a medical treatment, comprising:

a sheath having a first wall defining a first lumen therein, the first lumen having a distal end and being dimensioned to receive the previously implanted elongated medical apparatus therein, and being adapted to allow advancement of the sheath along the elongated medical apparatus, the sheath also having a second wall defining a second lumen therein, and a third wall defining a third lumen therein, said first wall non-overlapping with either of said second and third walls, said second and third lumens being generally parallel to said first lumen along a length of said sheath, said second and third lumens being positioned adjacent to each other along said sheath length; and a snare contained in the second lumen and the third lumen in the sheath, the snare having a snare loop extending out of the second lumen and the third lumen, at and generally extending around the distal end of the first lumen in the sheath, the snare loop being closeable about the elongated medical apparatus when the elongated medical apparatus is received in the first lumen of the sheath.

2. The device according to claim 1, wherein the sheath has a distal end, and a recess in the distal end receiving the snare loop therein.

3. The device according to claim 1, wherein the second lumen and the third lumen are coterminal with the sheath.

4. The device according to claim 1, wherein the second lumen and the third lumen are coterminal with the first lumen in the sheath.

5. The device according to claim 3, wherein the snare comprises one leg disposed in the second lumen and another leg disposed in the third lumen in the sheath.

6. The device according to claim 1, wherein the second lumen is coterminal with the sheath.

7. The device according to claim 1, wherein the second lumen is coterminal with the first lumen in the sheath.

8. The device according to claim 1, wherein the snare loop crosses over itself.

9. The device according to claim 1, wherein the snare includes a graspable pull opposite the snare loop.

10. The device according to claim 1, wherein the first, second and third lumens are unitarily formed in the sheath.

11. The device according to claim 1, wherein the second lumen in the sheath has a distal end, and wherein the snare loop depends generally perpendicularly from the distal end of the second lumen.

12. The device according to claim 1, wherein the snare is composed of a shape memory material.

13. The device according to claim 12, wherein the shape memory material of the snare is nitinol alloy.

14. The device according to claim 1, wherein the snare loop is positioned so as to draw the elongated structure against the wall of the sheath upon closure of the snare loop.

15. The device according to claim 1, wherein the sheath is tubular.

16. A device for removing a cardiac electrical lead implanted in biological tissue, comprising:

a sheath having a first wall defining a first lumen therein, the first lumen having a distal end and being dimensioned to receive the cardiac electrical lead therein, and being adapted to allow advancement of the sheath along the cardiac electrical lead; the sheath also having second and third walls defining second and third parallel lumens therein, the second and third lumens being coterminal with the first lumen and the sheath, and all of the first, second and third lumens being unitarily formed in the sheath, said second and third lumens being positioned within an arc of not greater than 90 degrees measured along a circumference of said sheath; and a snare contained in the second and third lumens in the sheath, the snare having a snare loop extending out of the second and third lumens at and generally extending around the distal end of the first lumen in the sheath;

wherein the snare comprises one leg disposed in the second lumen and another leg disposed in the third lumen, the legs being connected to the snare loop, and a graspable pull connected to the legs of the snare opposite the snare loop; and wherein the snare loop depends generally perpendicularly from distal ends of the second and third lumens, and is closeable about the cardiac electrical lead when the cardiac electrical lead is received in the first lumen of the sheath.

17. A device for removing an elongated medical apparatus previously implanted in biological tissue for a medical treatment, comprising:

a sheath having a proximal end and a distal end, said sheath having respective first, second, and third walls extending between said proximal end and said distal end along a length of said sheath, each of said first, second, and third walls defining a respective first, second, and third lumen, said walls spaced along said sheath length such that none of said first second and third walls overlaps another of said first, second and third walls along said sheath length, the first lumen having a distal end and being dimensioned to receive the previously implanted elongated medical apparatus therein; and a snare contained in the second lumen and the third lumen in the sheath, the snare defining a snare loop extending out of the second lumen and the third lumen, at and generally extending around the distal end of the first lumen in the sheath, the snare loop being closeable about the elongated medical apparatus when the elongated medical apparatus is received in the first lumen of the sheath.

18. The device of claim 17, wherein each of said lumens is generally circular.

19. The device of claim 17, wherein said second and third lumens are generally parallel to the first lumen along the length of said sheath.

\* \* \* \* \*

UNITED STATES PATENT AND TRADEMARK OFFICE
CERTIFICATE OF CORRECTION

PATENT NO. : 7,651,504 B2
APPLICATION NO. : 10/358512
DATED : January 26, 2010
INVENTOR(S) : Goode et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 970 days.

Signed and Sealed this

Twenty-third Day of November, 2010

David J. Kappos
*Director of the United States Patent and Trademark Office*